(12) United States Patent
McKinnon et al.

(10) Patent No.: US 9,126,012 B2
(45) Date of Patent: Sep. 8, 2015

(54) INTRAVENOUS CATHETER WITH DUCKBILL VALVE

(71) Applicants: Austin Jason McKinnon, Herriman, UT (US); Jeffrey Charles O'Bryan, Murray, UT (US)

(72) Inventors: Austin Jason McKinnon, Herriman, UT (US); Jeffrey Charles O'Bryan, Murray, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 307 days.

(21) Appl. No.: 13/644,163

(22) Filed: Oct. 3, 2012

(65) Prior Publication Data

US 2013/0090607 A1    Apr. 11, 2013

Related U.S. Application Data

(60) Provisional application No. 61/544,168, filed on Oct. 6, 2011.

(51) Int. Cl.
| | |
|---|---|
| *A61M 25/14* | (2006.01) |
| *A61M 25/00* | (2006.01) |
| *A61M 39/06* | (2006.01) |
| *A61M 25/06* | (2006.01) |
| *A61M 39/24* | (2006.01) |

(52) U.S. Cl.
CPC ....... *A61M 25/0097* (2013.01); *A61M 39/0693* (2013.01); *A61M 25/0606* (2013.01); *A61M 39/24* (2013.01); *A61M 2039/062* (2013.01); *A61M 2039/0646* (2013.01); *A61M 2039/242* (2013.01); *A61M 2039/2493* (2013.01)

(58) Field of Classification Search
CPC .. A61M 25/0074–25/0075; A61M 2025/0076; A61M 2025/0078; A61M 25/0097; A61M 25/0606; A61M 39/24; A61M 39/0693; A61M 2039/062; A61M 2039/2493; A61M 2039/242; A61M 2039/0646
USPC ................................ 604/247, 167.01–167.04
See application file for complete search history.

(56) References Cited

U.S. PATENT DOCUMENTS

| | | | |
|---|---|---|---|
| 4,387,879 | A | 6/1983 | Tauschinski |
| 4,449,693 | A | 5/1984 | Gereg |
| 4,758,225 | A | 7/1988 | Cox et al. |
| 4,773,552 | A | 9/1988 | Boege et al. |
| 4,781,702 | A | 11/1988 | Herrli |

(Continued)

FOREIGN PATENT DOCUMENTS

| | | |
|---|---|---|
| CA | 2 133 053 A1 | 3/1995 |
| DE | 20 2009 009 602 U1 | 12/2009 |

(Continued)

OTHER PUBLICATIONS

Elson Silva, PhD, "Respecting Hydrology Science in the Patenting System," pp. 1-7, Jan. 13, 2011.

*Primary Examiner* — Nicholas Lucchesi
*Assistant Examiner* — Justin L Zamory
(74) *Attorney, Agent, or Firm* — Jeanne Lukasavage; Craig Metcalf; Kirton McConkie

(57) ABSTRACT

A catheter assembly is disclosed, which includes a catheter adapter. A port is disposed in the catheter adapter to provide selective access to the interior of the catheter adapter, and can be used for fluid flushing or infusion. A valve is disposed within the catheter adapter that includes a one-way valve portion that prevents proximally-directed fluid flow. The valve further including a flexible tube portion that covers an opening between the port and the catheter adapter.

14 Claims, 9 Drawing Sheets

(56) References Cited

U.S. PATENT DOCUMENTS

| | | |
|---|---|---|
| 4,809,679 A | 3/1989 | Shimonaka et al. |
| 4,842,591 A | 6/1989 | Luther |
| 4,874,377 A | 10/1989 | Newgard et al. |
| 4,917,668 A | 4/1990 | Haindl |
| 4,935,010 A | 6/1990 | Cox et al. |
| 4,950,257 A | 8/1990 | Hibbs et al. |
| 5,041,097 A | 8/1991 | Johnson |
| 5,053,014 A | 10/1991 | Van Heugten |
| 5,062,836 A | 11/1991 | Wendell |
| 5,064,416 A | 11/1991 | Newgard et al. |
| 5,084,023 A | 1/1992 | Lemieux |
| 5,085,645 A | 2/1992 | Purdy et al. |
| 5,098,405 A * | 3/1992 | Peterson et al. ............ 604/247 |
| 5,108,374 A | 4/1992 | Lemieux |
| 5,127,905 A | 7/1992 | Lemieux |
| 5,154,703 A | 10/1992 | Bonaldo |
| 5,156,596 A | 10/1992 | Balbierz et al. |
| 5,176,652 A | 1/1993 | Littrell |
| 5,234,410 A | 8/1993 | Graham et al. |
| 5,269,771 A | 12/1993 | Thomas et al. |
| 5,290,246 A | 3/1994 | Yamamoto et al. |
| 5,295,969 A | 3/1994 | Fischell et al. |
| 5,330,435 A | 7/1994 | Vaillancourt |
| 5,350,363 A | 9/1994 | Goode et al. |
| 5,352,205 A | 10/1994 | Dales et al. |
| 5,405,323 A | 4/1995 | Rogers et al. |
| 5,456,675 A | 10/1995 | Wolbring et al. |
| 5,474,544 A | 12/1995 | Lynn |
| 5,487,728 A | 1/1996 | Vaillancourt |
| 5,520,666 A | 5/1996 | Choudhury et al. |
| 5,549,566 A | 8/1996 | Elias et al. |
| 5,549,577 A | 8/1996 | Siegel et al. |
| 5,575,769 A | 11/1996 | Vaillancourt |
| 5,613,663 A | 3/1997 | Schmidt et al. |
| 5,651,772 A | 7/1997 | Arnett |
| 5,657,963 A | 8/1997 | Hinchliffe et al. |
| 5,697,915 A | 12/1997 | Lynn |
| 5,730,418 A * | 3/1998 | Feith et al. ............. 251/149.6 |
| 5,738,144 A | 4/1998 | Rogers |
| 5,749,861 A | 5/1998 | Guala et al. |
| 5,776,096 A * | 7/1998 | Fields ............................. 604/43 |
| 5,806,831 A | 9/1998 | Paradis |
| 5,817,069 A | 10/1998 | Arnett |
| 5,833,674 A | 11/1998 | Turnbull et al. |
| 5,911,710 A | 6/1999 | Barry et al. |
| 5,954,698 A | 9/1999 | Pike |
| 5,967,490 A | 10/1999 | Pike |
| 6,039,302 A | 3/2000 | Cote, Sr. et al. |
| 6,077,244 A | 6/2000 | Botich et al. |
| 6,117,108 A | 9/2000 | Woehr et al. |
| 6,171,287 B1 | 1/2001 | Lynn et al. |
| 6,273,869 B1 | 8/2001 | Vaillancourt |
| 6,287,280 B1 | 9/2001 | Lampropoulos et al. |
| 6,485,473 B1 | 11/2002 | Lynn |
| 6,575,960 B2 | 6/2003 | Becker et al. |
| 6,595,981 B2 | 7/2003 | Huet |
| 6,699,221 B2 | 3/2004 | Vaillancourt |
| 6,719,726 B2 | 4/2004 | Meng et al. |
| 6,740,063 B2 | 5/2004 | Lynn |
| 6,883,778 B1 | 4/2005 | Newton et al. |
| 7,008,404 B2 * | 3/2006 | Nakajima .................. 604/158 |
| 7,347,839 B2 | 3/2008 | Hiejima |
| 7,396,346 B2 | 7/2008 | Nakajima |
| 7,470,254 B2 | 12/2008 | Basta et al. |
| 7,736,339 B2 | 6/2010 | Woehr et al. |
| 7,914,494 B2 | 3/2011 | Hiejima |
| 2006/0163515 A1 | 7/2006 | Ruschke |
| 2007/0083157 A1 | 4/2007 | Belley et al. |
| 2007/0083162 A1 | 4/2007 | O'Reagan et al. |
| 2007/0233007 A1 | 10/2007 | Adams |
| 2008/0039796 A1 | 2/2008 | Nakajima |
| 2008/0108944 A1 | 5/2008 | Woehr et al. |
| 2008/0287921 A1 | 11/2008 | Bennett |
| 2009/0287154 A1 | 11/2009 | Harding et al. |
| 2010/0204648 A1 | 8/2010 | Stout et al. |
| 2010/0204675 A1 | 8/2010 | Woehr et al. |
| 2010/0222746 A1 | 9/2010 | Burkholz |
| 2011/0046570 A1 | 2/2011 | Stout et al. |
| 2011/0160662 A1 | 6/2011 | Stout et al. |

FOREIGN PATENT DOCUMENTS

| | | |
|---|---|---|
| EP | 0 369 314 A2 | 5/1990 |
| EP | 0 440 426 A1 | 8/1991 |
| EP | 0 968 736 A1 | 1/2000 |
| EP | 1 129 740 A2 | 9/2001 |
| EP | 1 679 043 A1 | 7/2006 |
| WO | 93/11696 | 6/1993 |
| WO | 96/41649 | 12/1996 |
| WO | 98/00195 | 1/1998 |
| WO | 99/34849 | 7/1999 |
| WO | 99/38562 | 8/1999 |
| WO | 2006/037638 A1 | 4/2006 |
| WO | 2006/059540 A1 | 6/2006 |
| WO | 2007044878 A2 | 4/2007 |
| WO | 2008/014436 A2 | 1/2008 |
| WO | 2008/052790 A2 | 5/2008 |
| WO | 2009/114833 A1 | 9/2009 |
| WO | 2010/093791 A1 | 8/2010 |
| WO | 2012/002015 A1 | 1/2012 |

* cited by examiner

INTRAVENOUS CATHETER WITH DUCKBILL VALVE

RELATED APPLICATION

This application claims the benefit of U.S. Provisional Application No. 61/544,168 filed Oct. 6, 2011, entitled AN INTRAVENOUS CATHETER WITH DUCKBILL VALVE, which is incorporated herein by reference.

BACKGROUND

The current invention relates to intravenous (IV) infusion devices, including IV catheters. In particular, the invention relates to an IV catheter assembly having a blood control valve therein and an activator attachment that enables access to the interior of the IV catheter assembly.

IV catheters are commonly used for a variety of infusion therapies, including infusing fluids into a patient, withdrawing blood from a patient, or monitoring various parameters of the patient's vascular system. Catheters are typically connected to a catheter adapter that accommodates the attachment of IV tubing to the catheter. Blood control catheters include an internal blood control valve that is opened by the insertion of a male luer or other object into a proximal end of the catheter adapter. Non-limiting examples of blood control valves are disclosed in the United States Patent Application Publication No. 2011/0046570, filed Aug. 20, 2009, titled "Systems and Methods for Providing a Flushable Catheter Assembly," which is herein incorporated by reference in its entirety. Thus, following placement of the catheter into the vasculature of a patient, an IV fluid source can be connected to the catheter adapter, opening the blood control valve. Thus connected, fluid from the IV source can begin flow into a patient through the catheter.

Some catheter adapters permit verification of proper placement of the catheter in the blood vessel before fluid infusion begins, by providing a flashback chamber of the catheter assembly where a "flashback" of blood can be observed. To confirm flashback in catheter assemblies that do not include a blood control valve, a clinician must manually occlude the vein to prevent undesirable exposure to blood. In contrast, blood control valves can eliminate the need for such manual occlusion, while also reducing the likelihood of blood exposure during catheter placement.

Despite the many advantages of blood control catheters, some traditional procedures involving vascular access systems are not possible with blood control catheters. Devices and systems that overcome these deficiencies are disclosed herein.

BRIEF SUMMARY OF THE INVENTION

The present invention has been developed in response to problems and needs in the art that have not yet been fully resolved by currently available systems and methods. Thus, these systems and methods are developed to provide a valve within a catheter adapter that provides the dual function of a one-way valve through the lumen of the catheter adapter and a port valve.

In one aspect of the invention, a catheter assembly includes a catheter adapter, a port disposed on the catheter adapter, and a valve disposed within the catheter adapter. The catheter adapter has a proximal end, a distal end, and a lumen extending between the proximal end and the distal end. The port opens into the lumen. The valve is disposed within the lumen, and includes a flexible tube portion and a one-way valve portion. A portion of the flexible tube portion covers an opening between the port and the lumen. The one-way valve portion limits fluid flow through the valve to flow in a proximal direction.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" refers to a location on the device that is closest to the clinician using the device and farthest from the patient in connection with whom the device is used when the device is used in its normal operation. Conversely, the term "distal", "bottom", "down" or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

Figure 1:
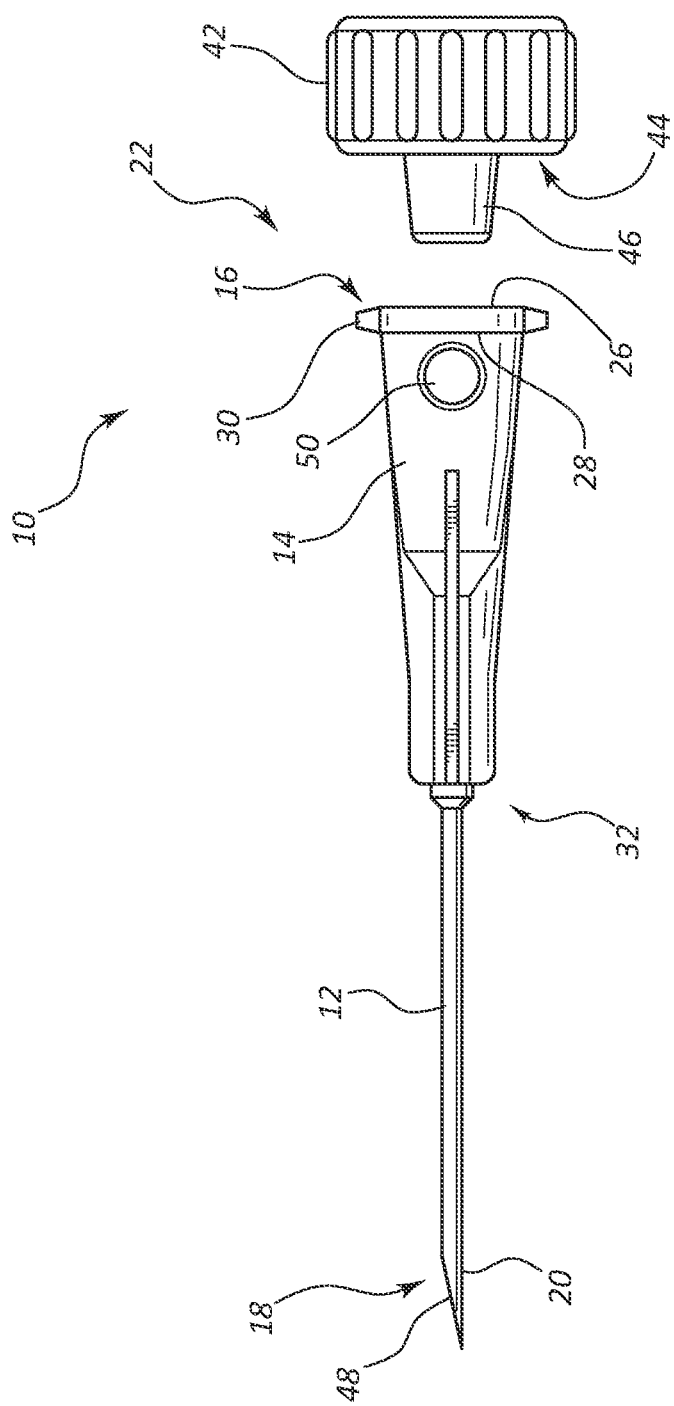
FIG. 1 is a perspective view of a catheter assembly having a port, according to some embodiments.

Referring now to FIG. 1, a catheter assembly 10 is illustrated, which generally includes a catheter 12 coupled to a distal end 32 of a catheter adapter 14. The catheter assembly 10 can be a blood control catheter assembly 10 when it includes a blood control valve therein. The catheter 12 and the catheter adapter 14 are integrally coupled such that an internal lumen 16 of the catheter adapter 14 is in fluid communication with a lumen 18 of the catheter 12. The catheter adapter 14 can include a port 50, which will be described in more detail with reference to FIG. 2. The catheter 12 generally comprises a biocompatible material having sufficient rigidity to withstand pressures associated with insertion of the catheter into a patient. A tip portion 20 of the catheter is generally configured to include a beveled cutting surface 48. The beveled cutting surface 48 is utilized to provide an opening in a patient to permit insertion of the catheter 12 into the vascular system of the patient.

One of skill in the art will appreciate that the features of the present invention may be incorporated for use with an over-the-needle catheter assembly, which can include the tapered end instead of a beveled cutting surface 48. For example, one of skill in the art will appreciate that a flexible or semi-flexible polymer catheter may be used in combination with a rigid needle to enable insertion of the catheter into a patient. One of skill in the art will further appreciate that surgically implanted catheters or other catheter types may also be used.

Once inserted into a patient, the catheter 12 and catheter adapter 14 provide a fluid conduit to facilitate delivery of a fluid to and/or retrieval of a fluid from a patient, as required by a desired infusion procedure. Thus, in some embodiments the material of the catheter 12 and the catheter adapter 14 are selected to be compatible with bio-fluids and medicaments commonly used in infusion procedures. Additionally, in some embodiments a portion of the catheter 12 and/or catheter adapter 14 is configured for use in conjunction with a section of intravenous tubing 40 to facilitate delivery of a fluid to or removal of a fluid from a patient.

In some embodiments, a proximal end 22 of the catheter adapter 14 includes a flange 28. The flange 28 provides a positive surface that may be configured to enable coupling of intravenous tubing or a conduit coupler 42 to the catheter assembly 10. In some embodiments, the flange 28 includes a set of threads 30. The threads 30 are generally provided and configured to compatibly receive a complementary set of threads 44 comprising a portion of a male luer or conduit coupler 42. The conduit coupler 42 is generally coupled to an end portion of the patient conduit in a fluid-tight manner. In some embodiments, an inner portion of the conduit coupler 42 is extended outwardly to provide a probe surface 46.

In some embodiments, the proximal end 22 to the catheter adapter 14 includes a female luer connector having a female luer taper and/or female luer lock threads. The female luer taper can be disposed at least in part within the proximal portion of the lumen 16 of the catheter adapter 14. Additionally, the flange 28 and/or threads 30 previously mentioned can comprise the female luer lock threads. The female luer connector can thus be configured to connect to a male luer lock or a male luer slip. Each of these components can be sized and configured in conformity with at least some of the International Standards Organization (ISO) standards for female and male luer connections under current or future standards. Accordingly, the proximal end 22 to the catheter adapter 14 can thus be configured to connect to a male luer lock or a male luer slip of the conduit coupler 42, IV line, luer access connector, needle hub, vent plug, or other known or future developed IV device.

Figure 4:
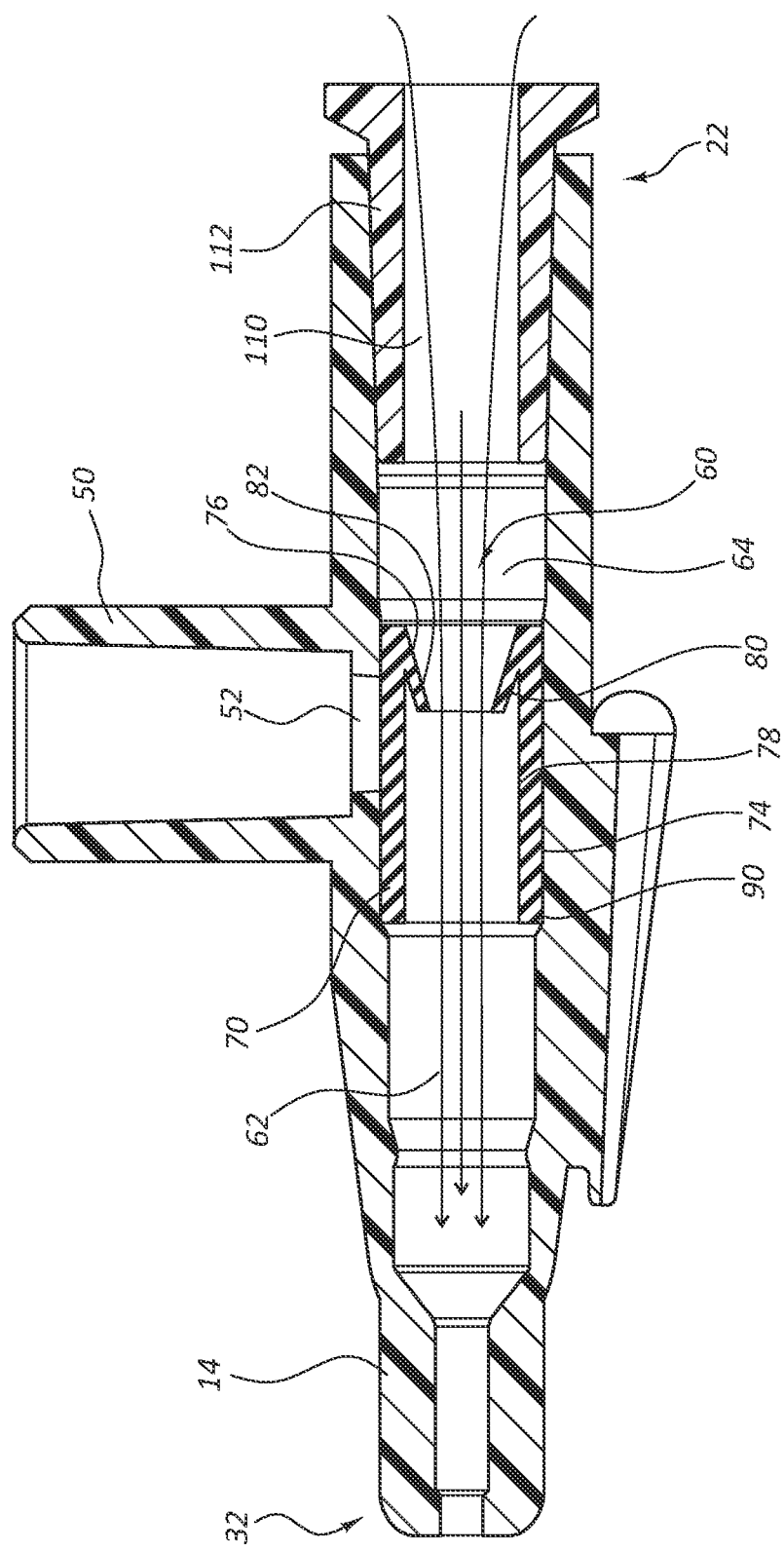
FIG. 4 is a cross-sectioned view of the catheter adapter of FIG. 2 connected to an infusion device, according to some embodiments.

The probe surface 46 is generally configured to compatibly insert within a proximal opening 26 in the proximal end 22 of the catheter adapter 14. Following insertion of the probe 46 into the proximal end 22 of the catheter adapter 14, the conduit coupler 42 is rotated to interlock the coupler 42 and the flange 28 (via the sets of threads 30 and 44). During the process of interlocking the coupler 42 and the flange 28, the probe 46 is advanced into the lumen 16 of the catheter adapter 14 to an inserted position (as shown in FIG. 4). The inserted position of the probe surface 46 activates the catheter assembly 10 to enable flow of fluid through the catheter 12 and catheter adapter 14. Once the conduit coupler 42 and the catheter adapter 14 are attached, a fluid may be delivered to a patient via the patient conduit 40 and the inserted catheter 12.

Figure 2:
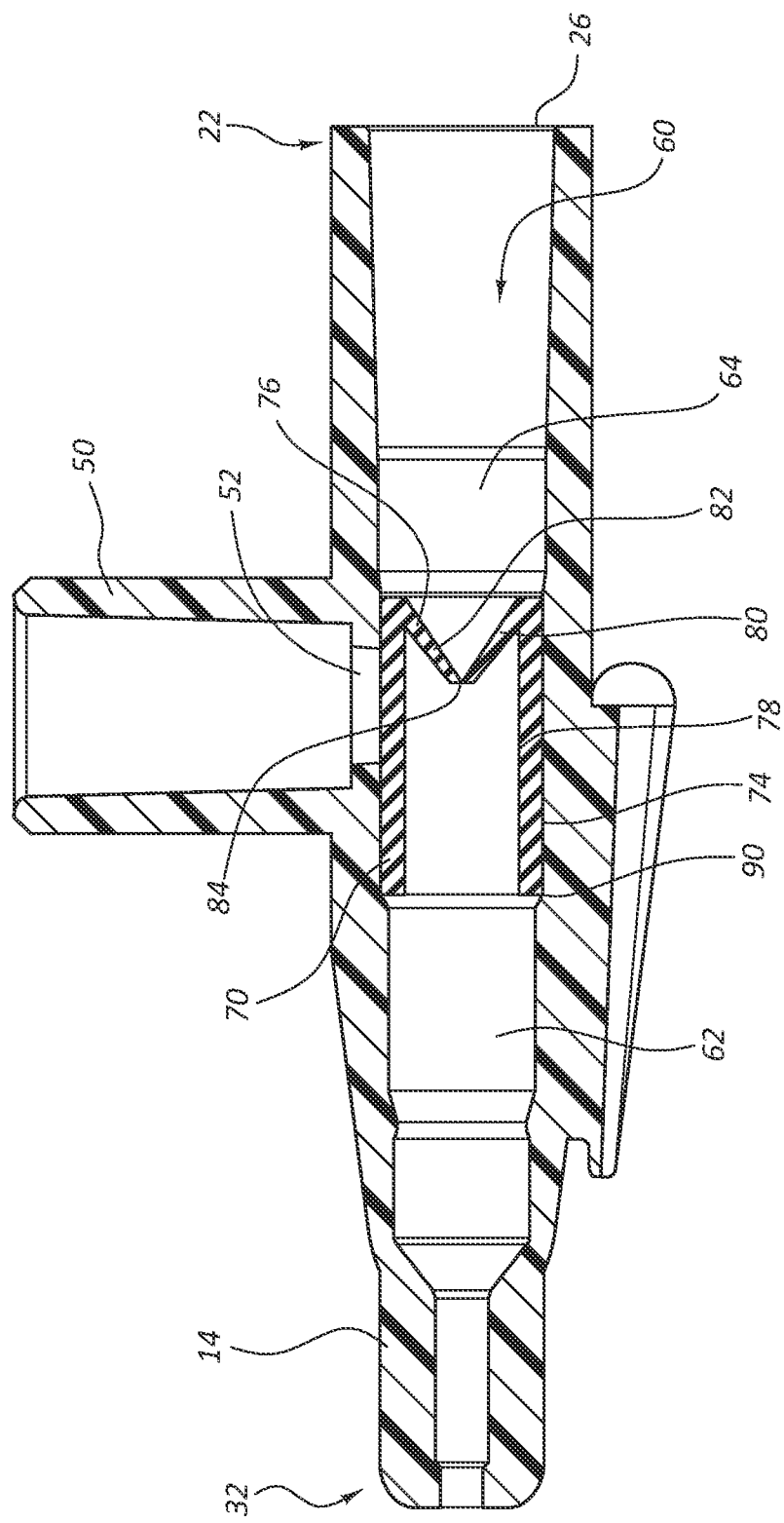
FIG. 2 is a cross-sectioned view of a catheter adapter having a valve, according to some embodiments.

Reference will now be made to FIG. 2, which depicts a cross-section view of the catheter adapter 14. As shown, the catheter adapter 14 can include a port 50, such as a side port. The port 50 can have various uses, including for the infusion of fluids into the internal lumen 60 of the catheter adapter 14. Such infusions can flush medicaments and other fluids from the internal lumen 60 and can be used to prime the catheter assembly 10. The port 50 can include an opening 52 disposed between the body of the port 50 and the internal lumen 60 of the catheter adapter 14. The body of the port 50 can extend away from the catheter adapter 14. In various embodiments, a port cover (not shown) selectively covers the port 50 to prevent contamination and exposure of port 50. Accordingly, in use, a clinician can open the port cover and infuse a fluid into the port 50 through the opening 52 into the internal lumen 60 of the catheter adapter 14. When the fluid infusion is complete, the clinician may close the port cover.

In some embodiments, the catheter adapter 14 includes a valve 70 that can serve the dual function of a selectively sealing both the port 50 and the internal lumen 60 of the catheter adapter 14. The valve 70 can divide the lumen 60 into a distal lumen chamber 62 and a proximal lumen chamber 64. In some embodiments, the valve 70 includes a one-way valve portion 76, such as the duckbill portion shown. In some embodiments, this one-way valve portion 76 allows flow in the distal direction, but resist flow, such as up to or more than a standard venous pressure (e.g., about 500 Pa to about 1500

Pa), the proximal direction. By resisting flow in the proximal direction, the valve 70 can prevent blood leakage out the proximal opening 26 of the catheter adapter 14. Moreover, the one-way valve portion 76 can have a minimal crack pressure in the distal direction, to allow fluid flow when fluid begins to be introduced into the proximal end 22 of the catheter adapter 14.

As shown in FIG. 2, the valve 70 can include a tube portion 78 and one-way valve portion 76. The tube portion 78 can have a generally tubular shape, including, but not limited to a cylindrically-shaped tube having a circular or semi-circular cross section. Other tubular configurations can include tubular shapes having other cross sections, including a triangle, square, pentagon, heptagon, octagon, other polygon, ellipses, oval, or other suitable cross sections. The tube portion 78 can extends longitudinally about a longitudinal axis of the catheter adapter 14. Moreover, the tube portion 78 can have outer dimensions that approximate the inner dimensions of the inner lumen 16 of the catheter adapter 14.

The one-way valve portion 76 can provide one-way valve functionality by limiting fluid flow in a single direction, such as the distal direction. As mentioned, the one-way valve portion 76 can be a duckbill valve, which can include two inwardly oriented flaps 80, 82, which are biased together toward a central position, forming a slit 84. The flaps 80, 82 can extend from the tube portion 78 inwardly and distally. Thus configured, the two inwardly oriented flaps 80, 82 can push together to close the valve in response to a fluid flow in a proximal direction (toward the distal end of the catheter adapter 14). Additionally, the two inwardly oriented flaps 80, 82 can be pushed apart to open a gap between these flaps 80, 82 in response to a fluid flow in a distal direction. As shown, the one-way valve portion 76 can be a duckbill style valve, while in other embodiments the one-way valve portion 76 can be any other pressure-activated valve that allows easy flow in the distal direction, but withstands venous pressure in the proximal direction (toward the proximal end of the catheter adapter 14).

In some embodiments, one-way valve portion 76 of the valve 70 is configured to open under the pressure of a fluid infusion through the proximal lumen opening 26 of the catheter adapter 14. As such, the one-way valve portion 76 can automatically open during fluid infusion and automatically close when the infusion stops. This ability can eliminate the need for a valve actuator that mechanically opens the valve.

In some embodiments, one or more slits 84 within the valve 70 permit passage of an introducer needle (not shown) through valve 70, thereby enabling a sharpened tip of the needle to extend distally beyond the tip portion 20 of the catheter 12. Following the catheterization procedure, the needle is removed from the catheter assembly 10 and is safely disposed.

In some embodiments, the needle is coated with a significant amount of silicone or similar fluid, such as fluorosilicone. The purpose of the coating fluid is threefold. Firstly, the coating fluid acts as a lubricant between the outer surface of the needle and the interfacing surfaces of slit 84. Thus, upon withdrawal of the needle from the valve 70, the coating fluid prevents undesirable adhesion between the outer surface of the needle and the interfacing surfaces of slit 84. Secondly, excess coating fluid accumulates within slit 84 thereby assisting in sealing the valve 70 to prevent blood from flowing back through the septum following removal of the needle. Excess coating fluid accumulates within slit 84 as needle is removed from catheter assembly 10. In particular, when the needle is being withdrawn through valve 70, the interfacing surfaces of slit 84 act to wipe the coating fluid from the outer surface of the needle thereby displacing the coating fluid into slit 84. Thirdly, the coating fluid acts as a lubricant to prevent undesirable adhesion between opposing surfaces of slit 84.

The coating fluid may include any biocompatible lubricant. In some embodiments, the coating fluid comprises a lubricant such as a non-wetting lubricant that is applied to an interface between the needle and the slit 84 to further eliminate possible leakage of fluid and/or air. A non-wetting lubricant may also be beneficial to prevent tearing or other damage to the slit that may occur when the needle is removed from the catheter assembly following catheterization. A non-wetting lubricant may also facilitate proper realignment of the opposing surfaces of slit 84 following removal of the needle. Non-limiting examples of a non-wetting lubricant include known Teflon based non-wetting materials such as Endura, from Endura Coating Co.; A20, E-20, 1000-S20, FEP Green, PTFE and X-40 from Tiodize; Cammie 2000 from AE Yale; 21845 from Ladd Research; MS122-22, MS122DF, MS-143DF, MS-122V MS-122VM, MS143V, MS-136W, MS-145W, U0316A2, U0316B2, MS-123, MS-125, MS-322 and MS-324 from Miller-Stepheson; and 633T2 from Otto Bock can also be used. Various non-Teflon based non-wetting lubricant type materials include Dylyn, from ART; Nyebar, Diamonex, NiLAD, TIDLN, Kiss-Cote, Titanium oxide; Fluocad Fluorochemical Coating FC-722, from 3M; Permacote from Dupont; Plasma Tech 1633 from Plasma Tech, Inc.; and silicone sprays.

Referring still to FIG. 2, in embodiments where the catheter adapter 14 includes a port 50, the valve 70 can function as a port valve. It will be understood that in other embodiments the catheter adapter 14 does not include a port 50. As shown, the tube portion 78 of the valve 70 can be positioned within the internal lumen 60 of the catheter adapter 14 such that an outer surface 74 of the tube portion 78 covers the opening 52 of the port 50. Thus positioned, the valve 70 can prevent fluid from within the lumen 76 from flowing out the port 50. Furthermore, the valve 70 can be configured to at least partially collapsed when fluid is introduced into the port 50, thus permitting fluid to pass through the opening 54 into the internal lumen 60 of the catheter adapter 14.

Valve 70 can be designed to at least partially collapse inwardly when a predetermined pressure is applied to the valve 70 from the opening 52 of the port 50. The predetermined pressure can be generally less than the amount of force pressing against valve 70 through the opening 54 during an infusion of fluid via the port 50. In various embodiments, the tube portion of the valve 70 is flexible or semi-flexible. The valve 70 can be made of various flexible or semi-flexible materials including, for example, silicone, silicone rubber, polypropylene, or other suitable materials. The flexibility or rigidity of the material can affect predetermined pressure required to open the valve 70 and allow fluid into the catheter adapter 14. A more flexible material may require a smaller predetermined pressure, while a more rigid material may require a greater predetermined pressure.

As shown, the tubular shape of the tube portion 78 of the valve 70 provides a channel within the body of the valve 70 can collapse under the predetermined pressure. The tubular shape can also provide structural strength that maintains the outer surface 62 of the valve 70 against the opening 52 of the port until the predetermined pressure is applied. The thickness of the walls of the tubular-shaped valve 70 can be selected to adjust the predetermined pressure required to open the valve 70. Thus, by increasing the thickness of the walls of the tube portion 78, a greater pressure is required to open the valve 70. By decreasing the wall thickness, a lesser pressure required. Additionally, the wall thicknesses can be adjusted based on the flexibility for rigidity the material forming the valve 70. For instance, a more rigid material may permit thinner walls that enable the same threshold force to open the port valve as a thicker wall made of a more flexible material. Accordingly, the flexibility of the valve 70 combined with the shape and size of the valve 70 can permit the valve 70 to collapse when a predetermined pressure is applied to the valve 70 via the opening 54.

In various embodiments, the valve 70 is seated within a groove or channel 90, which comprises a recessed portion of the inner surface of the catheter adapter 14. The outer diameter of the valve 70 can be generally configured to compatibly and securely seat within the groove or channel 90. For example, in some embodiments, the outer diameter of the valve 70 is selected to be both smaller than or approximately equal to the diameter of the groove or channel 90 and slightly larger than the diameter of the inner lumen 60. As such, the valve 70 can be retained within the groove or channel 90 during use of the catheter assembly 10. In other configurations, other features, such as protrusions on the proximal and distal ends of the valve 70 assist to retain the valve 70 in place.

As shown in FIG. 2, the catheter adapter 14 and dual-function valve 70 provides several beneficial features. For instance, the valve 70 does not require a valve actuator/activator to open as are required in blood control valves. This can reduce the number of components required. This same characteristic can permit the catheter adapter 14 to have a reduced length that it would need if it housed a valve actuator/activator. Additionally, since the valve 70 opens under pressure from the infusion line and automatically closes to pressure from the vein, it is re-useable.

Figure 3:
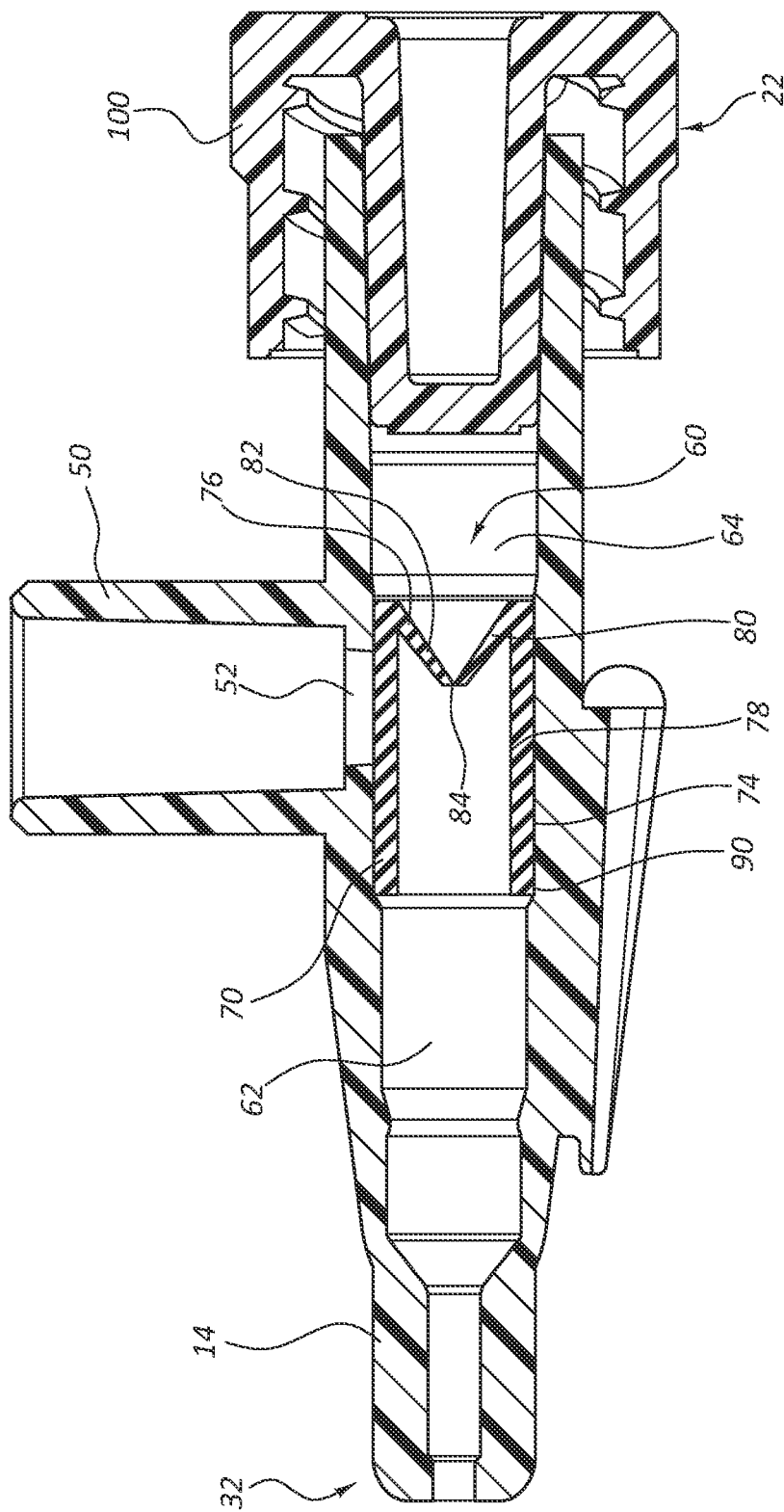
FIG. 3 is a cross-sectioned view of the catheter adapter of FIG. 2 having a cap, according to some embodiments.

As shown in FIG. 3, in some configurations, the proximal lumen opening 26 of the catheter adapter 14 can be closed with a cap 100 during a catheter flushing procedure or other procedure. The cap 100 can selectively attach to the proximal lumen opening 26 and close that opening. For instance, according to some medical customs, such as European medical customs, a cap 100 is attached to the proximal lumen opening 26 during an initial flushing of the catheter assembly 10 or for infusion to prevent fluid from flowing out the proximal opening 26 of the catheter adapter 14.

As shown in FIG. 4, as mentioned during an initial flushing procedure or fluid infusion, the one-way valve portion 76 of the valve 70 can be forced open by the fluid 110, which can allow passage of fluid 110 from fluid source 112 through the lumen 60 of the catheter adapter 14, in the distal direction. At the same time, the valve 70 can prevent fluid from escaping through the port 50. When the fluid source 112 is removed, the valve 70 can close in the absence of the force of the fluid. When closed, the one-way valve portion 76 can stop leakage of fluid and/or blood proximally past the valve 70. Additionally, as shown, during this type of fluid infusion, the tube portion 78 of the valve 70 can be maintained against the opening 52 of the port 50 to prevent the infused fluid 110 from exiting through this opening 52.

Figure 5:
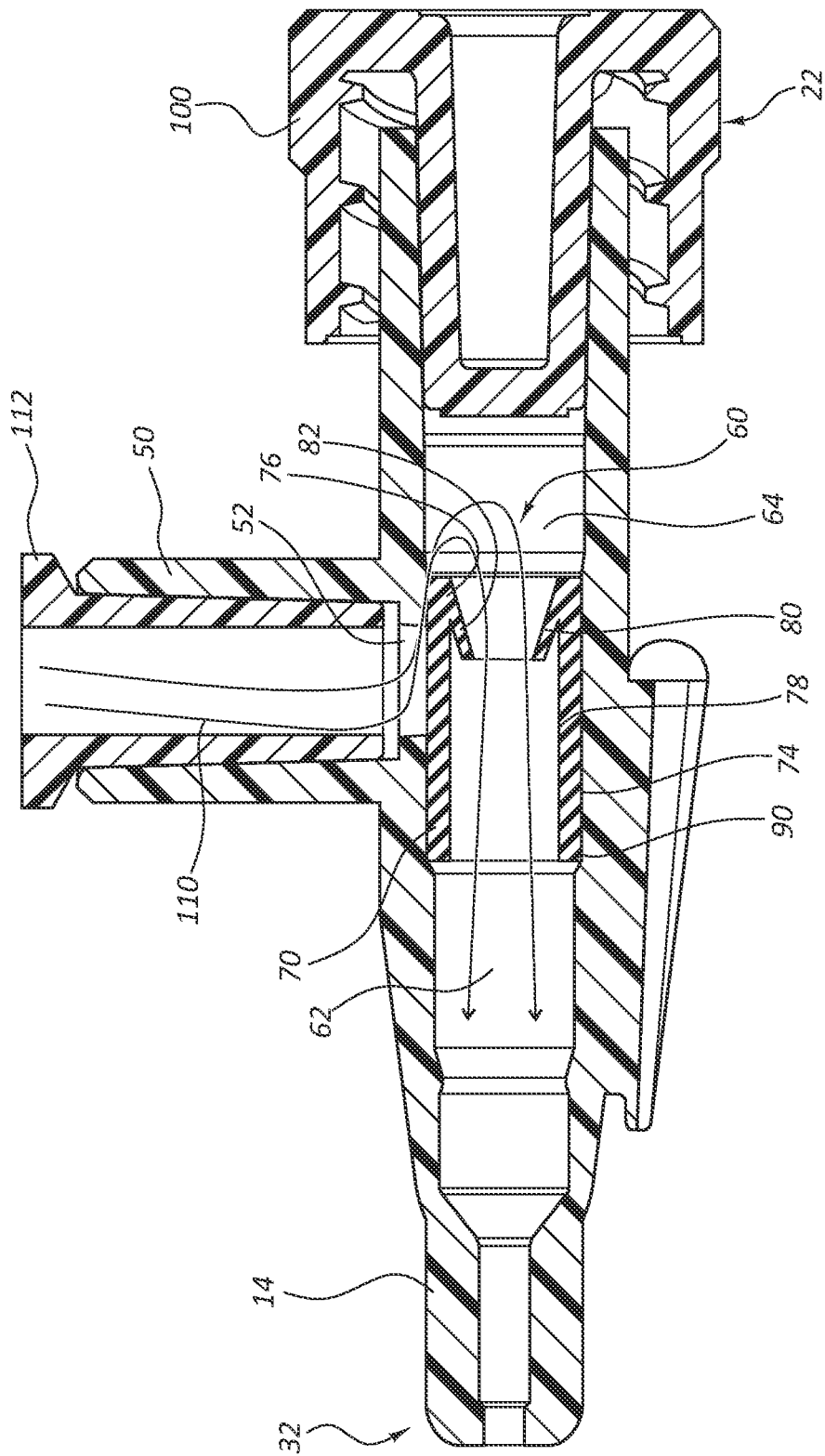
FIG. 5 is a cross-sectioned view of the catheter adapter and cap of FIG. 2 while fluid is infused through a side port, according to some embodiments.

As shown in FIG. 5, during an initial flushing procedure or for infusion through the port 50, fluid 110 can flow from the port 50 into the proximal lumen chamber 64. As fluid enters the proximal lumen chamber 64, the pressure within that chamber increases, opening the valve 70. As the valve 70 opens, fluid 110 can flow into the distal lumen chamber 62 and continue toward the patient.

As shown, the valve 70 and/or the catheter adapter 14 can be configured to force fluid 110 to the proximal side of the valve 70 rather than to the distal side of the valve 70 or to both sides simultaneously. Accordingly, the distal end of the valve 70 can form a seal with the inner surface of the catheter adapter 14. For example, the outer portions of the distal side of the valve 70 can be adhered to the inner surface of the catheter adapter 14 to form a seal about the distal end of the valve 70. In another example, the outer portions of the distal side of the valve 70 can have a larger outer diameter or other outer dimensions than the portions of the valve 70 proximal to that end. Similarly, the inner dimensions of the catheter adapter 14 about the distal side of the valve 70 can have a smaller inner diameter than the portions of the catheter adapter 14 proximal this area. These examples can form a tighter seal between the distal end of the valve 70 and the catheter adapter 14 that encourages fluid to flow into the proximal lumen chamber 64. In yet another example, the outer portions of the proximal side of the valve 70 can have a smaller outer diameter or other outer dimensions than the portions of the valve 70 distal to that end. Similarly, the inner dimensions of the catheter adapter 14 about the proximal side of the valve 70 can have a larger inner diameter than the portions of the catheter adapter 14 distal this area. These examples can form a weaker seal between the proximal end of the valve 70 and the catheter adapter 14 that encourages fluid to flow into the proximal lumen chamber 64.

Figure 6:
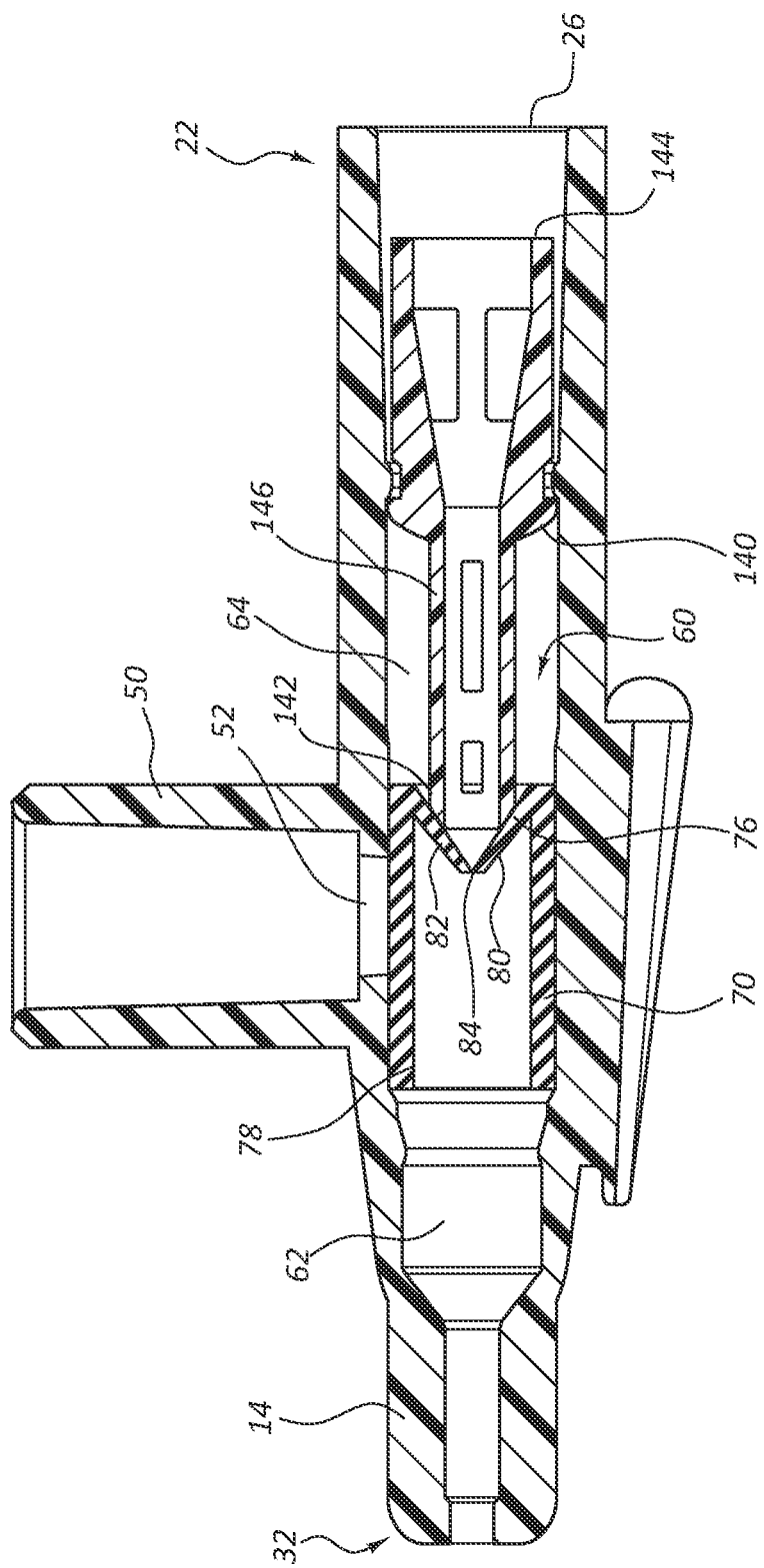
FIG. 6 is a cross-sectioned view of another catheter adapter having a valve and a valve activator, according to some embodiments.

As shown in FIG. 6, in some embodiments, the catheter adapter 14 includes a valve activator 140. The valve activator 140 can provide a mechanism within the catheter adapter 14 that has a proximal contact surface 144 that is contacted by a vascular access device inserted within the opening 26 of the catheter adapter 14. The vascular access device can push on the contract surface 144 to advance the valve activator 140 distally through the slit 84 of the valve 70 (shown in FIG. 9). As it moves distally forward, the probing surface 142 of the valve activator 140 pushes on the flaps 80, 82 of the one-way valve portion 76 to open the slit 84. The valve activator 140 can include a probe portion 146 that can have a cross section that is shaped and sized so that it can be inserted through the slit 84 of the valve 70. Moreover, the valve activator 140 can have various features, structures, and configurations, and can be moved and retained within the catheter adapter 14 as described in the United States Patent Application Publication No. 2011/0046570, filed Aug. 20, 2009, titled "Systems and Methods for Providing a Flushable Catheter Assembly," which is herein incorporated by reference in its entirety.

Figure 7:
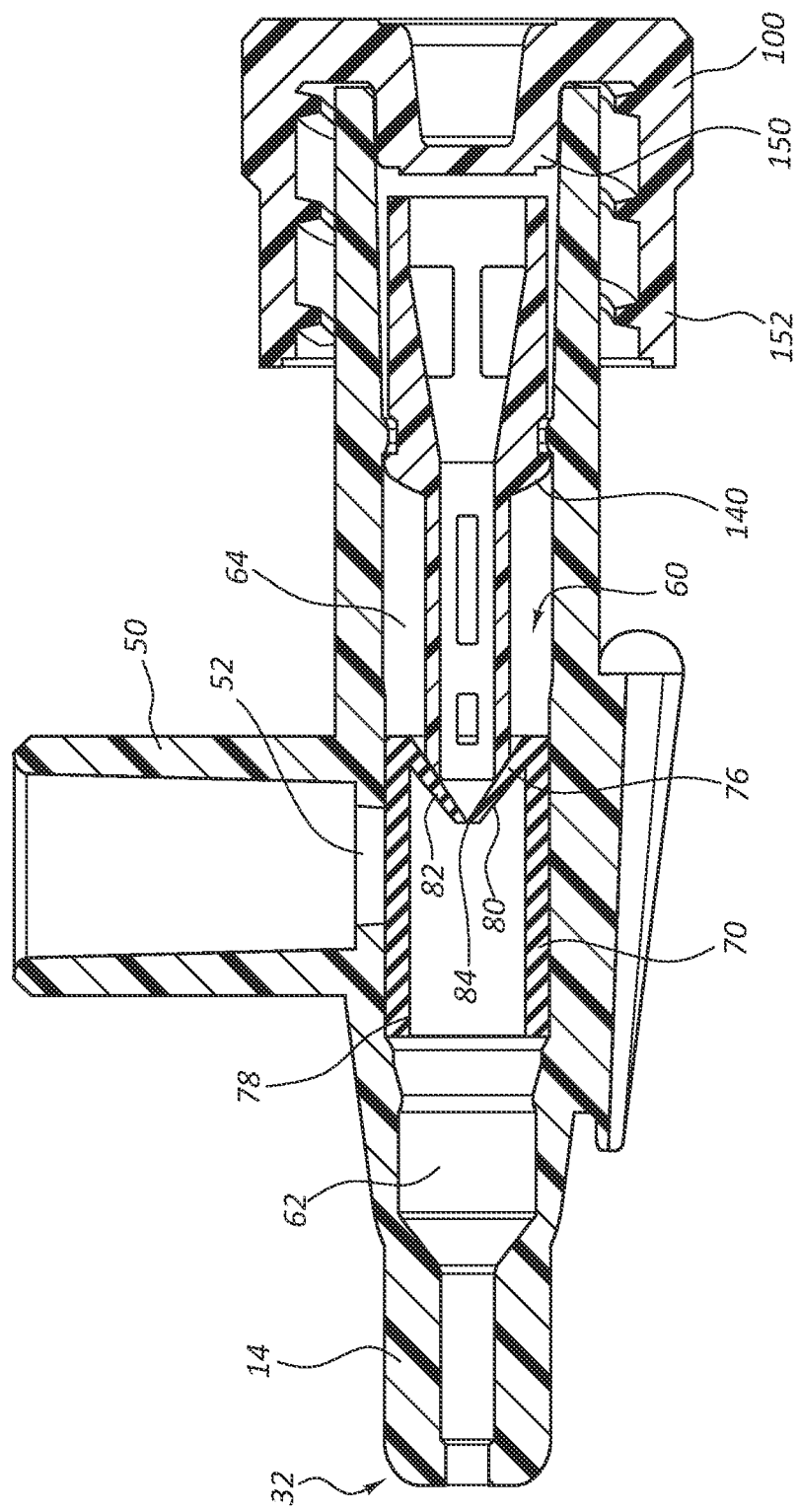
FIG. 7 is a cross-sectioned view of the catheter adapter of FIG. 6 having a cap, according to some embodiments.
Figure 8:
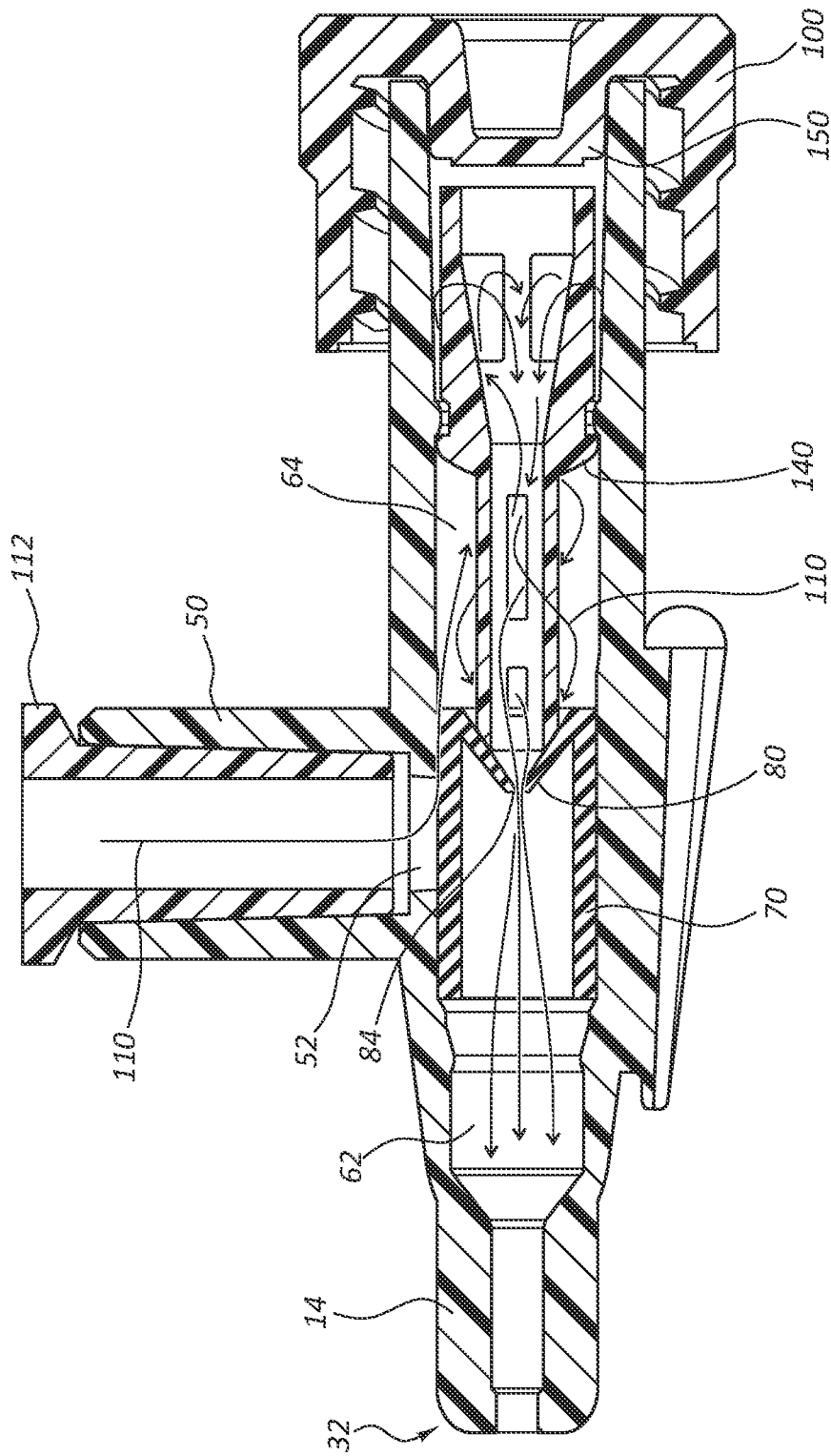
FIG. 8 is a cross-sectioned view of a catheter adapter and cap of FIG. 7 illustrating a flow path of fluid entering the side port, according to some embodiments.

As shown in FIGS. 7 and 8, in embodiments having a valve activator 140, a cap 100 can be provided that has truncated male luer 150. In some configurations, the cap 100 can include a truncated male luer 150 that is not long enough to advance the valve activator 140 to open the valve 70. For example, the male luer collar 152 of the cap can extend farther than the truncated male luer 150 within this collar 152. As shown in FIG. 8, when the cap 100 is attached the proximal end 22 of the catheter adapter 14, fluid 110 entering the port 50 can flush the proximal lumen chamber 64 about the valve activator 140 and subsequently passed through the valve 70.

Figure 9:
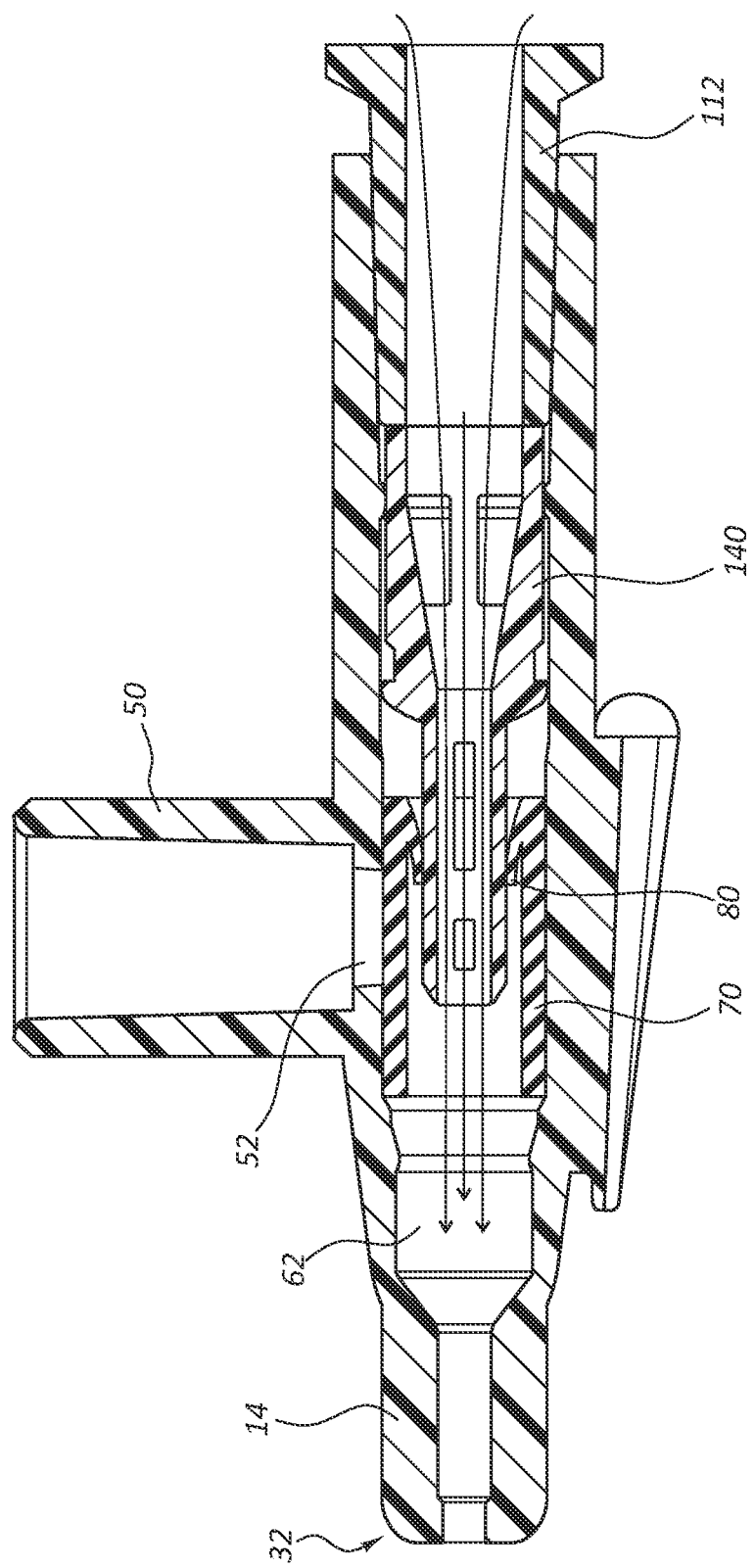
FIG. 9 is a cross-sectioned view of a catheter adapter of FIG. 6 with the valve activator moved to an activated position, according to some embodiments.

As shown in FIG. 9, when a separate device 112 is inserted into the proximal lumen opening 26 of the catheter adapter 14, the valve activator 140 can be distally advanced through the slit 84 of the valve 70, opening the valve 70. In this manner, the valve 70 can be opened when the catheter adapter 14 is connected to a separate device 112, such as an IV infusion device.

The present catheter assembly 10 can provide a number of benefits. For example, present catheter assembly can be flushed through the side/top port 50. Since flushing can originate from the side port, and a cap 100 can be maintained on the proximal end of the catheter adapter 14 until the first IV set connection is made, which fully opens the valve for infusion. Thus, the catheter assembly can remain closed and sterile for a longer period. Present catheter assembly 10 can also reduce the number of components and assembly steps required.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter assembly comprising:
    a catheter adapter having a proximal end, a distal end, and a lumen extending between the proximal end and the distal end, the catheter adapter further comprising an inner surface;
    a port disposed in the catheter adapter, an interior of the port being in fluid communication with the lumen;
    a valve disposed within the lumen, the valve including a flexible tube having a distal end and a proximal end, an interior of the flexible tube further comprising a one-way valve dividing the lumen of the catheter adapter into a proximal lumen and a distal lumen, an outer surface of the flexible tube covering an opening between the interior of the port and the lumen of the catheter adapter;
    a first flow pathway through the lumen of the catheter adapter, the interior of the flexible tube, and the one-way valve in a distal direction;
    a second flow pathway between an outer surface of the proximal end of the flexible tube and the inner surface of the catheter adapter in a proximal direction;
    a fluid-tight seal interposed between an outer surface of the distal end of the flexible tube and the inner surface of the catheter adapter; and
    a defeatable seal interposed between the outer surface of the proximal end of the flexible tube and the inner surface of the catheter adapter, wherein the defeatable seal and the second flow pathway allow fluid flow from the port into the proximal lumen, and the one-way valve and first flow pathway allow fluid flow from the proximal lumen to the distal lumen.

2. The catheter assembly of claim 1, wherein the flexible tube is substantially cylindrical.

3. The catheter assembly of claim 1, wherein the one-way valve is a duckbill valve disposed on the proximal end of the flexible tube.

4. The catheter assembly of claim 3, wherein the valve is configured to prevent blood flow under venous pressure in a proximal direction through the one-way valve.

5. The catheter assembly of claim 3, wherein the one-way valve includes two or more flaps coupled to the flexible tube of the valve, the two or more flaps extending inwardly and distally from the flexible tube.

6. The catheter assembly of claim 1, wherein the proximal end of the flexible tube is configured to partially collapse inwardly when a fluid pressure increases within the interior of the port.

7. The catheter assembly of claim 1, wherein the valve is disposed within a channel of the inner surface of the catheter adapter.

8. The catheter assembly of claim 1, further comprising a separate vascular access device having a probe for insertion into a proximal opening of the catheter adapter, the probe having a length sufficient to pass through a slit of the one-way valve to provide a pathway therethrough.

9. The catheter assembly of claim 8, wherein the probe includes a proximal dimension that approximates an inner dimension of the lumen.

10. The catheter assembly of claim 8, wherein the probe includes an activator shaped and sized for insertion through the one-way valve.

11. The catheter assembly of claim 1, further comprising a valve activator disposed within the proximal lumen, the valve activator having a probe portion configured to be inserted through the one-way valve to provide a pathway therethrough.

12. The catheter assembly of claim 11, further comprising a cap having a truncated male luer.

13. A catheter assembly system comprising:
    a catheter adapter having a proximal end, a distal end, and a lumen extending between the proximal end and the distal end, the catheter adapter further comprising an inner surface;
    a port disposed in the catheter adapter, an interior of the port being in fluid communication with the lumen;
    a valve disposed within the lumen, the valve including a flexible tube having a distal end and a proximal end, an interior of the flexible tube further comprising a one-way valve dividing the lumen of the catheter adapter into a proximal lumen and a distal lumen, an outer surface of the flexible tube covering an opening between the interior of the port and the lumen of the catheter adapter;
    a first flow pathway through the lumen of the catheter adapter, the interior of the flexible tube, and the one-way valve in a distal direction;
    a second flow pathway between an outer surface of the proximal end of the flexible tube and the inner surface of the catheter adapter in a proximal direction;
    a fluid-tight seal interposed between an outer surface of the distal end of the flexible tube and the inner surface of the catheter adapter; and
    a defeatable seal interposed between the outer surface of the proximal end of the flexible tube and the inner surface of the catheter adapter, the defeatable seal and the second flow pathway being configured to allow fluid flow from the port into the proximal lumen chamber, and the one-way valve and the first flow pathway being configured to allow fluid flow from the proximal lumen to the distal lumen; and
    a valve activator disposed within the proximal lumen, the valve activator having a probe configured to be inserted through the one-way valve of the valve.

14. The catheter assembly of claim 13, wherein the flexible tube of the valve has a substantially cylindrical shape, the one-way valve is a duckbill valve, the one-way valve of the valve being disposed on the proximal end of the flexible tube, and the one-way valve of the valve being configured to withstand at least an average venous pressure in a proximal direction from the distal end to the proximal end.

* * * * *